United States Patent [19]

Rempfler

[11] 4,326,880
[45] Apr. 27, 1982

[54] DERIVATIVES OF 5-(PYRIDYL-2-OXY)-2-NITROBENZOIC ACID, AND HERBICIDAL COMPOSITIONS CONTAINING THEM, AND HERBICIDAL METHODS FOR USING SAME

[75] Inventor: Hermann Rempfler, Ettingen, Switzerland

[73] Assignee: Ciba-Geigy Corporation, Ardsley, N.Y.

[21] Appl. No.: 174,985

[22] Filed: Aug. 4, 1980

[30] Foreign Application Priority Data

Aug. 14, 1979 [CH] Switzerland ..................... 7430/79

[51] Int. Cl.³ .................... C07D 213/64; A01N 43/40
[52] U.S. Cl. ....................................... 71/94; 546/291; 546/300; 546/194; 544/360
[58] Field of Search ............................ 546/300; 71/94

[56] References Cited

U.S. PATENT DOCUMENTS 4,213,774  7/1980  Schurter et al ..................... 546/300
4,235,621  11/1980  Nishiyama et al. ................. 546/300

FOREIGN PATENT DOCUMENTS 2753900  6/1978  Fed. Rep. of Germany ........ 560/21

Primary Examiner—Alan L. Rotman
Attorney, Agent, or Firm—Frederick H. Rabin

[57] ABSTRACT

The invention relates to 5-(pyridyl-2'-oxy)-2-nitrobenzoic acid derivatives of the formula

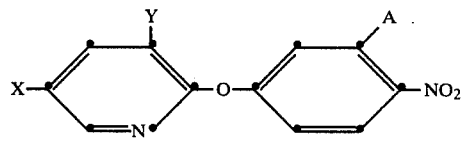

wherein A is the cyano group, the carboxyl group or a salt, an ester, a thioester or an amide thereof, X is halogen or a halomethyl group, Y is hydrogen, halogen or a halomethyl group. These compounds have herbicidal properties and are suitable for selectively controlling weeds in crops of useful plants, especially in soybeans, cereals and rice crops.

13 Claims, No Drawings

DERIVATIVES OF 5-(PYRIDYL-2'-OXY)-2-NITROBENZOIC ACID, AND HERBICIDAL COMPOSITIONS CONTAINING THEM, AND HERBICIDAL METHODS FOR USING SAME

The present invention relates to novel derivatives of 5-(pyridyl-2'-oxy)-2-nitrobenzoic acid which have herbicidal properties, processes for the production of these novel acid derivatives, compositions containing them as active ingredients, and their use as herbicides, especially as selective herbicides in crops of useful plants.

The derivatives of 5-(pyridyl-2'-oxy)-2-nitrobenzoic acid are novel compounds. Derivatives of 3-(p-trifluoromethylphenoxy)-6-nitrobenzoic acid having herbicidal properties are known from U.S. Pat. No. 3,928,416 and German Offenlegungsschrift No. 2 753 900. Herbicidal 3-(p-trifluoromethylphenoxy)-6-nitrobenzoic acid derivatives are disclosed in U.S. Pat. No. 4,031,131 and, finally, herbicidal 3-(phenoxy)-6-nitrobenzoic acid derivatives are known from U.S. Pat. No. 3,784,635.

The derivatives of 5-(pyridyl-2'-oxy)-nitrobenzoic acid have the formula

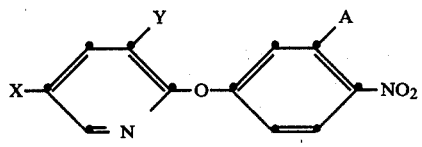

wherein X is halogen or a halomethyl group, Y is hydrogen, halogen or a halomethyl group, A is the cyano group, a radical —COB or a 2-oxazoline radical which is unsubstituted or substituted by one or more methyl groups, B is a radical —OR$_1$, —SR$_2$, —NR$_3$R$_4$ or —ON=C(R$_5$)$_2$, wherein R$_1$ is hydrogen or the cation of a base (1/n) M$^{n\oplus}$, wherein M is an alkali metal cation or an alkaline earth metal cation or an iron, copper, zinc or

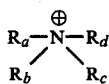

cation, n as 1, 2 or 3 corresponds to the valency of the cation, whilst each of R$_a$, R$_b$, R$_c$ and R$_d$ independently is hydrogen, benzyl, or a C$_1$-C$_4$alkyl radical which can be substituted by —OH, —NH$_2$ or C$_1$-C$_4$alkoxy; R$_1$ and R$_2$ are a C$_1$-C$_{18}$alkyl radical which is unsubstituted or substituted by halogen, nitro, cyano, C$_1$-C$_8$alkoxy, C$_2$-C$_8$alkoxyalkoxy, oxirane, C$_3$-C$_6$alkenyloxy, C$_1$-C$_8$alkylthio, C$_2$-C$_8$alkanoyl, C$_2$-C$_8$acyloxy, C$_2$-C$_8$alkoxycarbonyl, carbamoyl, C$_1$-C$_4$alkylamino, bis(C$_1$-C$_4$alkyl) amino, C$_2$-C$_4$alkenylamino, bis(C$_2$-C$_4$alkenyl)amino, C$_2$-C$_4$-alkynylamino, bis(C$_2$-C$_4$alkynyl)amino, tris(C$_1$-C$_4$alkyl)ammonio, C$_3$-C$_8$cycloalkyl, C$_3$-C$_8$cycloalkenyl, or also by a phenyl, phenoxy or 5- or 6-membered heterocyclic radical containing 1 to 3 heteroatoms, each of which is unsubstituted or is itself mono- or polysubstituted by halogen, C$_1$-C$_4$alkyl or C$_1$-C$_4$alkoxy; or is a C$_3$-C$_{10}$alkenyl radical which is unsubstituted or mono- to tetrasubstituted by halogen or monosubstituted by phenyl or methoxycarbonyl; as C$_3$-C$_8$alkynyl radical; a C$_3$-C$_{12}$cycloalkyl radical which is unsubstituted or substituted by halogen or C$_1$-C$_4$alkyl; a C$_3$-C$_8$cycloalkylene radical, a phenyl radical which is unsubstituted or mono- or polysubstituted by halogen, C$_1$-C$_4$alkyl, C$_1$-C$_4$alkoxy, C$_1$-C$_4$alkylthio, NO$_2$, CF$_3$, COOH, CN, OH, SO$_3$H, NH$_2$ or —NH(C$_1$-C$_4$alkyl) or —N(C$_1$-C$_4$alkyl)$_2$; a 5- or 6-membered heterocyclic ring containing 1 to 3 hetero-atoms; and each of R$_3$ and R$_4$ is hydrogen, a C$_1$-C$_4$-alkyl radical which is unsubstituted or substituted by C$_1$-C$_4$alkoxy, hydroxyl, halogen or C$_2$-C$_8$alkoxycarbonyl, a C$_3$-C$_5$alkenyl radical, a C$_3$-C$_5$alkynyl radical, a C$_3$-C$_7$cycloalkyl radical or an aromatic radical, or one of R$_3$ and R$_4$ is also a C$_1$-C$_4$alkoxy or C$_1$-C$_4$alkylsulfonyl radical, or R$_3$ and R$_4$, together with the nitrogen atom to which they are attached, are also a 5- or 6-membered heterocyclic ring system which can contain an additional oxygen or sulfur atom or an imino group which is unsubstituted or substituted by C$_1$-C$_3$alkyl, and each R$_5$ is C$_1$-C$_4$alkyl or both together form a C$_3$-C$_5$alkylene chain.

In formula I, halogen denotes fluorine, chlorine, bromine or iodine

The term "alkyl" by itself or as moiety of a substituent comprises branched or unbranched alkyl groups, e.g. methyl, ethyl, propyl, isopropyl, butyl, isobutyl, sec-butyl, tert-butyl and the higher homologues amyl, isoamyl, hexyl, heptyl, octyl etc. together with their isomers.

The alkenyl and alkynyl radicals also comprise branched and unbranched radicals which contain the indicated number of carbon atoms and at least one unsaturated position. Preferred alkenyl radicals are the unsubstituted or halogen-substituted allyl, methallyl and n-butenyl radicals. The preferred alkynyl radical is the propynyl of propargyl radical.

Cycloalkyl radicals are cyclopropyl, cyclobutyl, cyclopentyl, cyclohexyl and cycloheptyl. Cycloalkenyl radicals correspond to these ring systems, but where possible, additionally contain one or more double bonds.

Heterocyclic rings contain 1 to 3 identical or different heteroatoms O, S and N. Examples are in particular 5- or 6-membered heterocyclic ring systems which are saturated, partially saturated or unsaturated and which can be substituted. Without any limitation being implied, examples are: furane, nitrofurane, bromofurane, methylfurane, thiophene, chlorothiophene, pyridine, 2,6-dichloropyridine, pyrimidine, pyridazine, pyrazine, piperidine, methylpiperidine, methylpiperidine, morpholine, thiomorpholine, tetrahydrofurane, oxazole, pyrazole, pyrrole, pyrroline, pyrrolidine, thiazole, 2,3-dihydro-4H-pyrane, pyrane, dioxane, 1,4-oxathi-(2)-ine.

The compounds (active ingredients) of the formula I have in general pronounced selective herbicidal activity and are especially advantageous for controlling weeds in crops of useful plants, particularly in crops of soybeans, cotton, cereals, rice, maize and sugar beet. When employed in sufficiently high rates of application, however, the compounds of the formula I also act as total herbicides. Application can be both pre- and post-emergence. The rates of application can vary within wide limits, e.g. from 0.1 to 10 kg of active ingredient per hectare. However, it is preferred to employ from 0.5 to 5 kg of active ingredient per hectare.

Compounds belonging structurally to the following groups are very effective against weeds in crops of wheat, rice and/or soybeans:

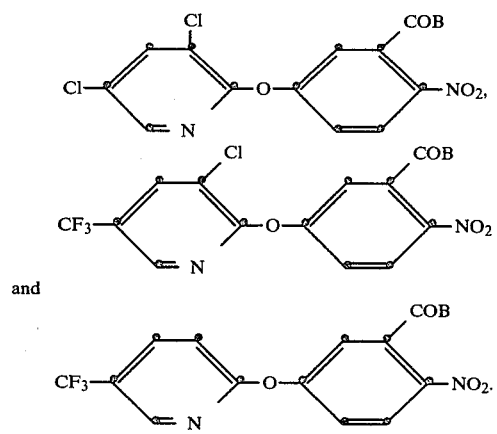

In these compounds, B can have in general any meaning within the definition given for formula I. The most active compounds are those in which B is hydroxyl, $C_1$-$C_{18}$-alkoxy, $C_1$-$C_4$cyanoalkoxy, $C_3$-$C_{18}$alkoxycarbonylalkyl, di($C_1$-$C_4$alkyl)amino-$C_1$-$C_4$alkyl, $C_3$-$C_{10}$alkenyl, $C_3$-$C_{10}$alkynyl, $C_1$-$C_{18}$alkylthio, $C_3$-$C_{18}$alkoxycarbonylalkylthio, $C_3$-$C_{10}$alkenylthio, $C_1$-$C_4$alkylamino, $C_2$-$C_8$alkoxyalkylamino, $C_3$-$C_8$alkoxycarbonylalkylamino or N-$C_1$-$C_4$alkoxy-N-$C_1$-$C_4$alkylamino.

In addition to containing the active ingredients of the formula I, the compositions of this invention contain a suitable carrier and/or other adjuvants. Suitable carriers and adjuvants can be solid or liquid and correspond to the substances customarily employed in the art of formulation, e.g. natural or regenerated mineral substances, solvents, diluents, dispersants, emulsifiers, wetting agents, tackifiers, thickeners, binders and/or fertilisers.

For use in herbicidal compositions, the compounds of the formula I can be processed to dusts, emulsifiable concentrates, granules, dispersions or also to solutions or suspensions in conventional formulation.

The compositions of the present invention are obtained in known manner by intimately mixing and grinding active ingredients of the general formula I with suitable carriers and/or adjuvants, with or without the addition of antifoams, wetting agents, dispersants and/or solvents which are inert to the active ingredients. The active ingredients can be processed to the following formulations:

solid formulations: dusts, tracking powders, granules (coated granules, impregnated granules and homogeneous granules);
active ingredient concentrates which are dispersible in water: wettable powders, pastes, emulsions, emulsifiable concentrates;
liquid formulations: solutions.

The concentrations of active ingredient in the compositions of this invention are between 1 and 80 percent by weight. As circumstances may require, the active ingredients can also be applied in low concentrations of about 0.05 to 1 percent by weight.

The compositions of the present invention can be mixed with other biocidal compounds or compositions. Thus in addition to containing the compounds of the general formula I, the compositions of the invention can also contain e.g. insecticides, fungicides, bactericides, fungistatic agents, bacteriostatic agents, nematocides or further herbicides, in order to broaden the activity spectrum.

The compounds of the formula I are obtained by methods which are known per, for example by one of the following synthesis routes.

One convenient process for obtaining the 5-(pyridyl-2'-oxy)-2-nitrobenzoic acid derivatives of the formula I comprises reacting a 2-halopyridine of the formula II

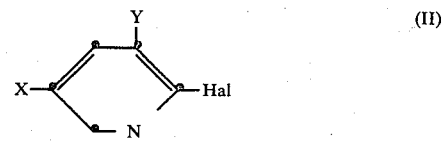

wherein Hal is halogen and X and Y have the given meanings, in an organic solvent and in the presence of a base, with a 3-hydroxy-6-nitrobenzoic acid derivative of the formula III

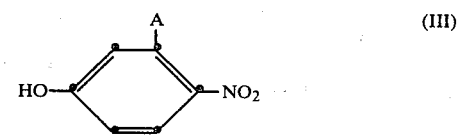

wherein A is a radical as defined under formula I.

Another synthesis route consists in reacting the 2-halopyridine of the formula II and a 3-hydroxy-benzoic acid derivative of the formula IV

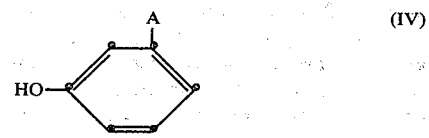

wherein A is a radical as defined under formula I, initially in an aprotic solvent and in the presence of a base which acts as acid acceptor, to give the 3-(pyridyl-2'-oxy)-benzoic acid derivative of the formula V

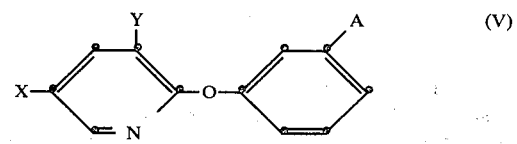

wherein A, X and Y have the given meanings.

The second process for obtaining the compounds of formula I comprises nitrating a 3-(pyridyl-2'-oxy)-benzoic acid derivative of the above formula V with a nitrating acid mixture.

Finally, in compounds of the formula I in which A is e.g. the acid nitrile, a carboxyl group or the carboxamide, it is possible to convert these radicals by appropriate reactions such as saponification, esterification, amination, or alkylation, to other carboxylic acid derivatives falling under the definition of A.

These reactions are carried out in the temperature range from 0° to 150° C. Suitable solvents are in particular aprotic solvents such as dimethyl sulfoxide, dimethyl formaldehyde, sulfolane, N-methyl-pyrrolidone etc.

Suitable bases which are added to bind the eliminated halogen atom are both inorganic bases such as alkali metal hydroxides and carbonates and bicarbonates of alkali metals and alkaline earth metals, and organic bases, e.g. alkylamines such as dimethylamine, trimethylamine, diethylamine, triethylamine etc.

Examples of nitrating solutions are mixtures of nitric and sulfuric acid, solutions of nitric acid in glacial acetic acid, or concentrated nitric acid by itself, e.g. in chlorinated hydrocarbons. The nitration reactions are carried out in the temperature range from about 0° C. to room temperature.

The compounds of the formula I are stable compounds which have low mammalian toxicity and no precautionary measures are necessary for handling them. They have relatively good solubility in customary organic solvents and are reluctantly soluble in water.

The following Examples illustrate in more detail the production of the 5-(pyridyl-2'-yl-oxy)-2-nitrobenzoic acids of the formula I. Further compounds obtained in analogous manner are listed in the subsequent table. Parts and percentages are by weight and pressures are indicated in millibars.

EXAMPLE 1
5-(3'-Chloro-5'-trifluoromethylpyridyl-2'-oxy)-2-nitrobenzoic acid

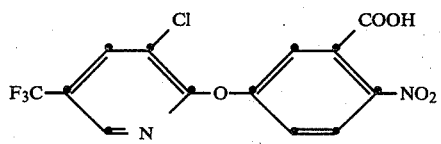

8.4 g of 5-(3'-chloro-5'-trifluoromethylpyridyl-2'-oxy) benzoic acid are suspended in 100 ml of ethylene chloride and the suspension is cooled. Then 18 ml of concentrated sulfuric acid and a solution of 1.5 ml of 100% nitric acid in 18 ml. of 2.5 ml of sulfuric acid are added dropwise in succession. The reaction mixture is stirred for 2 hours at room temperature and then poured into 100 ml of icewater. The organic phase is separated and the aqueous phase is extracted with ethylene chloride. The ethylene chloride extract is dried over magnesium sulfate and concentrated. The residue is crystallised by trituration with petroleum ether. The crystals are collected by filtration, affording 5.6 g (60% of theory) of the title compound with a melting point of 114°–117° C.

The starting 5-(3'-chloro-5'-trifluoromethyl-pyridyl-2'-oxy)-benzoic acid is prepared as follows:

A solution of 5.8 g (0.042 mole) of 3-hydroxybenzoic acid in 15 ml of dimethyl sulfoxide is added dropwise to a suspension of 2 g (0.084 mole) of sodium hydride in 15 ml of dimethyl sulfoxide. When all the sodium hydride is dissolved, a solution of 8.3 g of 2-fluoro-2-chloro-5-trifluoromethylpyridine in 10 ml of dimethyl sulfoxide is added dropwise, whereupon the temperature rises to 45° C. The reaction is complete after stirring for 6 hours at 85° C. The dimethyl sulfoxide is evaporated off in vacuo and the residue is poured into ice-water. Acidification with hydrochloric acid results in the formation of a precipitate, which is collected by filtration and washed with water. Recrystallisation from ethanol/water yields 8.4 g (63% of theory) of pure 3-(3'-chloro-5'-trifluoromethylpyridyl-2'-oxy)benzoic acid with a melting point of 141°–145° C.

EXAMPLE 2
2-Nitro-5-(3',5'-dichloropyridyl-2'-oxy)-2-benzonitrile

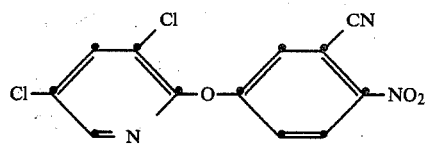

A solution of 16.4 g (0.1 mole) of 3-cyano-4-nitrophenol in 50 ml of N-methylpyrrolidone is added dropwise to a suspension of 2.4 g (0.1 mole) of sodium hydride in 30 ml of N-methylpyrrolidone. When the evolution of hydrogen has ceased, 16.6 g (0.1 mole) of 2-fluoro-3,5-dichloropyridine are added. The reaction mixture is stirred for 15 hours at 110°–115° C. and then poured into ice-water. The water is extracted with chloroform and the chloroform extract is dried over sodium sulfate and concentrated. The residue is purified over a column of silica gel with ethyl acetate/hexane as eluant, affording 6.2 g (30% of theory) of the title compound with a melting point of 138°–140° C.

EXAMPLE 3
Methyl 2-nitro-5-(3',5'-dichloropyridyl-2'-oxy) benzoate

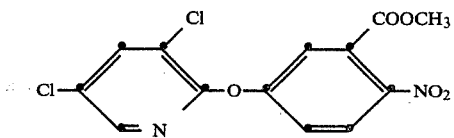

6.6 g of 2-nitro-5-(3',5'-dichloropyridyl-2'-oxy) benzoic acid (prepared according to Example 1) are mixed with 10 ml of thionyl chloride and the mixture is stirred for 15 hours at 60° C. Excess thionyl chloride is removed by evaporation. The residue is dissolved in 50 ml of toluene and to this solution are added 1 g of methanol and 2.1 g of triethylamine. The salt is collected by filtration after 1 hour and the filtrate is concentrated. The residue is crystallised from ethyl acetate and hexane, affording 4 g (62% of theory) of the title compound with a melting point of 81°–82° C.

The following compounds are obtained by procedures analogous to those described in the foregoing Examples:

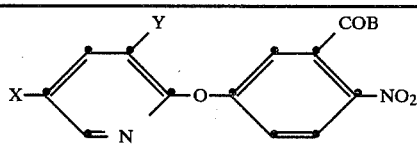

| No. | X | Y | B | Physical data (°C.) |
|---|---|---|---|---|
| 1 | Cl | Cl | OH | m.p. 166–169° |
| 2 | Cl | Cl | OCH$_3$ | m.p. 81–82° |
| 3 | Cl | Cl | OC$_2$H$_5$ | |
| 4 | Cl | Cl | OC$_3$H$_7$n | |
| 5 | Cl | Cl | OC$_3$H$_7$iso | n$_D^{25}$ 1.5815 |
| 6 | Cl | Cl | OC$_4$H$_9$n | |
| 7 | Cl | Cl | OC$_4$H$_9$sec | n$_D^{30}$ 1.5840 |
| 8 | Cl | Cl | OC$_4$H$_9$iso | n$_D^{25}$ 1.5680 |
| 9 | Cl | Cl | OC$_4$H$_9$tert | |
| 10 | Cl | Cl | OC$_5$H$_{11}$iso | n$_D^{27}$ 1.5675 |
| 11 | Cl | Cl | OCHC$_3$H$_7$ with CH$_3$ branch | n$_D^{27}$ 1.5677 |

-continued

[Structure: X-pyridine(Y)-O-phenyl(COB)(NO2)]

| No. | X | Y | B | Physical data (°C.) |
|---|---|---|---|---|
| 12 | Cl | Cl | $OCH(C_2H_5)_2$ | |
| 13 | Cl | Cl | $OCH_2CH_2OCH_3$ | |
| 14 | Cl | Cl | $OCH_2CH_2OC_2H_5$ | |
| 15 | Cl | Cl | $OCH_2CH_2OC_4H_9$ | $n_D^{27}$ 1.5620 |
| 16 | Cl | Cl | $OCH_2CH$—$CH_2$ (epoxide) | |
| 17 | Cl | Cl | $OCH_2CH_2N(CH_3)_2$ | $n_D^{30}$ 1.5817 |
| 18 | Cl | Cl | $OCH_2CH_2N$(morpholine) | |
| 19 | Cl | Cl | $OCH(CH_3)COOCH_3$ | $n_D^{27}$ 1.5605 |
| 20 | Cl | Cl | $O(CH_2)_3N(CH_3)_2$ | |
| 21 | Cl | Cl | $OCH_2CH=CH_2$ | |
| 22 | Cl | Cl | $OCH_2CH=CH\,CH_3$ | $n_D^{25}$ 1.5877 |
| 23 | Cl | Cl | $OCH_2C\equiv CH$ | m.p. 81–82° |
| 24 | Cl | Cl | $OCH_2C\equiv C$—$CH_3$ | |
| 25 | Cl | Cl | $OC(CH_3)(C\equiv CH)CH=CH_2$ | |
| 26 | Cl | Cl | O-tetrahydropyranyl-$C\equiv CH$ | |
| 27 | Cl | Cl | $OCH_2CN$ | $n_D^{27}$ 1.5890 |
| 28 | Cl | Cl | $OCH_2CH_2Cl$ | |
| 29 | Cl | Cl | $OCH_2CH_2Br$ | |
| 30 | Cl | Cl | $NH_2$ | m.p. 179–180° |
| 31 | Cl | Cl | $NHCH_3$ | |
| 32 | Cl | Cl | $NHC_2H_5$ | m.p. 119–120° |
| 33 | Cl | Cl | $NHC_3H_7(iso)$ | |
| 34 | Cl | Cl | $NHCH_2CH=CH_2$ | |
| 35 | Cl | Cl | $NHCH_2C\equiv CH$ | |
| 36 | Cl | Cl | $NHC_4H_9(sec)$ | |
| 37 | Cl | Cl | $NH(C_2H_5)_2$ | |
| 38 | Cl | Cl | $NHCH_2COOCH_3$ | |
| 39 | Cl | Cl | $N(CH_3)_2$ | |
| 40 | Cl | Cl | $N(C_2H_5)_2$ | |
| 41 | Cl | Cl | morpholino | |
| 42 | Cl | Cl | NH-pyrazinyl | |
| 43 | Cl | H | OH | m.p. 166–169° |
| 44 | Cl | H | $OCH_3$ | |
| 45 | Cl | H | $OC_2H_5$ | |
| 46 | Cl | H | $N(CH_3)_2$ | |
| 47 | Cl | H | $NHCH_2COOC_2H_5$ | |
| 48 | Cl | Cl | NH-pyrrolyl | |
| 49 | Cl | H | NHCH$_2$-pyrrolyl | |
| 50 | Cl | Cl | $SCH_3$ | |
| 51 | Cl | Cl | $SC_2H_5$ | $n_D^{27}$ 1.6200 |
| 52 | Cl | Cl | $SC_4H_9(iso)$ | $n_D^{27}$ 1.5965 |
| 53 | Cl | Cl | $SCH_2CH=CH_2$ | |
| 54 | Cl | Cl | $SCH_2COOCH_3$ | $n_D^{27}$ 1.6060 |
| 55 | Cl | Cl | $SCH_2C\equiv CH$ | |
| 56 | Cl | Cl | $SCH_2C\equiv CCH_3$ | |
| 57 | Cl | Br | OH | |
| 58 | Cl | Br | $OCH_3$ | |
| 59 | Cl | Br | $OC_2H_5$ | |
| 60 | Cl | Br | $OC_5H_9(iso)$ | |
| 61 | Cl | Br | $OC_4H_9(sec)$ | |
| 62 | Cl | Br | $SC_3H_7(n)$ | |
| 63 | Cl | Br | $SC_4H_9(n)$ | |
| 64 | Cl | Br | $SCH_2CH=CH_2$ | |
| 65 | Cl | Br | $OCH(CH_2)_4$ | |
| 66 | Cl | Br | $OCH_2CH(CH_2)_5$ | |
| 67 | Cl | Br | $NHC_2H_5$ | |
| 68 | Cl | Br | $NHC_3H_7(iso)$ | |
| 69 | Cl | Br | $NHC_8H_{17}$ | |
| 70 | Cl | Br | $N(CH_2CH=CH_2)_2$ | |
| 71 | Br | Cl | OH | |
| 72 | Br | Cl | $OCH_3$ | |
| 73 | Br | Cl | $OC_2H_5$ | |
| 74 | Br | Cl | $OC_3H_7(iso)$ | |
| 75 | Br | Cl | $OC_4H_9(sec)$ | |
| 76 | Br | Cl | $OC_4H_9(iso)$ | |
| 77 | Br | Cl | $OC_4H_9(tert)$ | |
| 78 | Br | Cl | $OCH(CH_2CH_3)_2$ | |
| 79 | Br | Cl | $OCH(CH_3)C_3H_7$ | |
| 80 | Br | Cl | $SCH_3$ | |
| 81 | Br | Cl | $SC_3H_7$ | |
| 82 | $CF_3$ | Cl | OH | m.p. 114–117° |
| 83 | $CF_3$ | Cl | $OCH_3$ | $n_D^{25}$ 1.5357 |
| 84 | $CF_3$ | Cl | $OC_2H_5$ | |
| 85 | $CF_3$ | Cl | $OC_3H_7(n)$ | |
| 86 | $CF_3$ | Cl | $OC_3H_7(iso)$ | $n_D^{30}$ 1.5278 |
| 87 | $CF_3$ | Cl | $OC_4H_9(n)$ | |
| 88 | $CF_3$ | Cl | $OC_4H_9(iso)$ | $n_D^{20}$ 1.5225 |
| 89 | $CF_3$ | Cl | $OC_4H_9(sec)$ | $n_D^{30}$ 1.5265 |
| 90 | $CF_3$ | Cl | $O(CH_2)_4Cl$ | $n_D^{30}$ 1.5350 |
| 91 | $CF_3$ | Cl | $OC_5H_{11}(n)$ | |
| 92 | $CF_3$ | Cl | $OCH(CH_3)C_3H_7$ | $n_D^{30}$ 1.5174 |
| 93 | $CF_3$ | Cl | $OCH(C_2H_5)_2$ | |
| 94 | $CF_3$ | Cl | $OCH_2CH_2CH(CH_3)_2$ | |
| 95 | $CF_3$ | Cl | $OC_6H_{13}(n)$ | |
| 96 | $CF_3$ | Cl | $OC_7H_{15}(n)$ | |
| 97 | $CF_3$ | Cl | $OCH(CH_3)C_5H_{11}(n)$ | |
| 98 | $CF_3$ | Cl | $OC_8H_{17}(n)$ | $n_D^{30}$ 1.5125 |
| 99 | $CF_3$ | Cl | $OCH_2CH_2Cl$ | $n_D^{30}$ 1.5485 |
| 100 | $CF_3$ | Cl | $OCH_2CH_2Br$ | |
| 101 | $CF_3$ | Cl | $OCH_2CH_2F$ | |
| 102 | $CF_3$ | Cl | $OCH_2CH_2OCH_3$ | $n_D^{30}$ 1.5365 |
| 103 | $CF_3$ | Cl | $OCH_2CH_2OC_4H_9$ | |
| 104 | $CF_3$ | Cl | $OCH_2CH_2OC_2H_5$ | |
| 105 | $CF_3$ | Cl | $OCH_2CN$ | m.p. 100–102° |
| 106 | $CF_3$ | Cl | $OCH(CH_3)COOCH_2CH_3$ | $n_D^{30}$ 1.5213 |
| 107 | $CF_3$ | Cl | $OCH_2CH=CH_2$ | $n_D^{30}$ 1.5411 |
| 108 | $CF_3$ | Cl | $OCH_2CH=CHCH_3$ | |
| 109 | $CF_3$ | Cl | $OCH_2C(CH_3)=CH_3$ | |
| 110 | $CF_3$ | Cl | $OCH_2C\equiv CH$ | m.p. 94–96° |
| 111 | $CF_3$ | Cl | $OCH(CH_3)$—$C\equiv CH$ | |
| 112 | $CF_3$ | Cl | $O(CH_3)_2C\equiv CH$ | |
| 113 | $CF_3$ | Cl | O-tetrahydropyranyl-$C\equiv CH$ | |
| 114 | $CF_3$ | Cl | $OCH_2CH$—$CH_2$ (epoxide) | |

-continued

Structure:
$$\text{X-pyridine(Y)-O-phenyl(COB)(NO}_2\text{)}$$

| No. | X | Y | B | Physical data (°C.) |
|---|---|---|---|---|
| 115 | CF₃ | Cl | ON=C(CH₃)₂ | m.p. 89-91° |
| 116 | CF₃ | Cl | O-furyl | |
| 117 | CF₃ | Cl | O-furyl-Br | m.p. 92-94° |
| 118 | CF₃ | Cl | OCH₂-furyl-Cl | m.p. 79-81° |
| 119 | CF₃ | Cl | OCH₂CH₂N(CH₃)₂ | $n_D^{30}$ 1.5336 |
| 120 | CF₃ | Cl | OCH₂CH₂N(morpholino) | |
| 121 | CF₃ | Cl | OCH₂CH₂N(piperazinyl)N—CH₃ | |
| 122 | CF₃ | Cl | SCH₃ | $n_D^{30}$ 1.5695 |
| 123 | CF₃ | Cl | SC₂H₅ | |
| 124 | CF₃ | Cl | SC₃H₇(n) | |
| 125 | CF₃ | Cl | SC₃H₇(iso) | $n_D^{30}$ 1.5590 |
| 126 | CF₃ | Cl | SC₄H₉(n) | |
| 127 | CF₃ | Cl | SC₄H₉(iso) | |
| 128 | CF₃ | Cl | SC₅H₁₁(n) | |
| 129 | CF₃ | Cl | SCH₂COOCH₃ | $n_D^{30}$ 1.5650 |
| 130 | CF₃ | Cl | SCH₂CH=CH₂ | $n_D^{30}$ 1.5725 |
| 131 | CF₃ | Cl | SCH₂C≡CH | |
| 132 | CF₃ | Cl | SCH₂CH=CHCH₃ | |
| 133 | CF₃ | Cl | SCH₂C(CH₃)=CH₂ | |
| 134 | CF₃ | Cl | S-thienyl | |
| 135 | CF₃ | Cl | SCH₂-furyl | $n_D^{30}$ 1.5972 |
| 136 | CF₃ | Cl | NHCH₃ | m.p. 139-42° |
| 137 | CF₃ | Cl | NHC₂H₅ | |
| 138 | CF₃ | Cl | NHC₃H₇(iso) | |
| 139 | CF₃ | Cl | NHC₄H₉(n) | |
| 140 | CF₃ | Cl | NHC₄H₉(iso) | |
| 141 | CF₃ | Cl | NHC₅H₁₁(n) | |
| 142 | CF₃ | Cl | NHCH(C₂H₅)₂ | |
| 143 | CF₃ | Cl | NHC₈H₁₇(n) | |
| 144 | CF₃ | Cl | NHCH₂CH₂Cl | |
| 145 | CF₃ | Cl | NHCH₂CH₂OH | |
| 146 | CF₃ | Cl | NHCH₂CH₂OCH₃ | |
| 147 | CF₃ | Cl | NHCH₂CH₂OC₄H₉ | |
| 148 | CF₃ | Cl | NHCH₂COOC₂H₅ | |
| 149 | CF₃ | Cl | NHCH₂C≡CH | |
| 150 | CF₃ | Cl | NHCH₂CH=CH₂ | |
| 151 | CF₃ | Cl | NHC(CH₃)₂≡CH | |
| 152 | CF₃ | Cl | NHC(CH₃)₂CN | |
| 153 | CF₃ | Cl | NH-furyl | |
| 154 | CF₃ | Cl | NHCH₂-furyl | |
| 155 | CF₃ | Cl | N(CH₃)₂ | |
| 156 | CF₃ | Cl | N(C₂H₅)₂ | $n_D^{30}$ 1.5352 |
| 157 | CF₃ | Cl | N(CH₂CH=CH₂)₂ | |
| 158 | CF₃ | Cl | N-pyrrolyl | |
| 159 | CF₃ | Cl | N-O-morpholino | |
| 160 | CF₃ | Cl | NH₂ | |
| 161 | CF₃ | Cl | S⁻K⁺ | |
| 162 | CF₃ | Cl | S⁻Na⁺ | |
| 163 | CF₃ | Cl | O⁻H₃N⁺C₃H₇(iso) | |
| 164 | CF₃ | H | OH | m.p. 139-144° |
| 165 | CF₃ | H | OCH₃ | |
| 166 | CF₃ | H | OC₂H₅ | |
| 167 | CF₃ | H | OC₃H₇(n) | |
| 168 | CF₃ | H | OC₄H₉(iso) | |
| 169 | CF₃ | H | OC₄H₉(sec) | |
| 170 | CF₃ | H | OCHC₃H₇\|CH₃ | |
| 171 | CF₃ | H | SCH₃ | |
| 172 | CF₃ | H | SC₂H₅ | |
| 173 | CF₃ | H | SC₃H₇(iso) | |
| 174 | CF₃ | H | SC₄H₉(iso) | |
| 175 | CF₃ | H | SC₅H₁₁ | |
| 176 | CF₃ | H | NH₂ | |
| 177 | CF₃ | H | NHCH₃ | |
| 178 | CF₃ | H | NHC₂H₅ | |
| 179 | CF₃ | H | NHC₃H₇(iso) | |
| 180 | CF₃ | H | NHC₄H₉(n) | |
| 181 | CF₃ | H | NHC₆H₁₃ | |
| 182 | CF₃ | H | NHCH₂CH₂Cl | |
| 183 | CF₃ | H | NHCH₂CH₂OCH₃ | |
| 184 | CF₃ | H | NHCH₂C≡CH | |
| 185 | CF₃ | H | NHCH₂C≡CH | |
| 186 | CF₃ | H | NHCH₂COOCH₃ | |
| 187 | CF₃ | H | NH-phenyl-Cl,Cl | |
| 188 | CF₃ | H | N(CH₃)₂ | |
| 189 | CF₃ | H | N(CH₂CH=CH₂)₂ | |
| 190 | H | CF₃ | OH | |
| 191 | H | CF₃ | OCH₃ | |
| 192 | H | CF₃ | OC₂H₅ | |
| 193 | H | CF₃ | OC₄H₉(iso) | |
| 194 | H | CF₃ | SCH₃ | |
| 195 | H | CF₃ | SCH₂CH=CH₂ | |
| 196 | H | CF₃ | SC₄H₉(n) | |
| 197 | H | CF₃ | NHCH₃ | |
| 198 | H | CF₃ | NHC₂H₅ | |
| 199 | H | CF₃ | NHC₄H₉(iso) | |
| 200 | Cl | CF₃ | OH | |
| 201 | Cl | CF₃ | OCH₃ | |
| 202 | Cl | CF₃ | OC₂H₅ | |
| 203 | Cl | CF₃ | OC₃H₇(iso) | |
| 204 | Cl | CF₃ | OCH₂CH₂OCH₃ | |
| 205 | Cl | CF₃ | SCH₃ | |
| 206 | Cl | CF₃ | NHCH₃ | |
| 207 | Cl | CF₃ | NHC₂H₅ | |
| 208 | Cl | CF₃ | N(CH₃)₂ | |
| 209 | Cl | CF₃ | N(CH₂CH=CH₂)₂ | |
| 210 | CCl₂F | Cl | OH | |
| 211 | CCl₂F | Cl | OCH₃ | |
| 212 | CCl₂F | Cl | OC₂H₅ | |
| 213 | CCl₂F | Cl | OC₃H₇(n) | |
| 214 | CCl₂F | Cl | OC₃H₇(iso) | |
| 215 | CCl₂F | Cl | OC₄H₉(iso) | |
| 216 | CCl₂F | Cl | OC₄H₉(sec) | |
| 217 | CCl₂F | Cl | OCH₂CH₂OCH₃ | |
| 218 | CCl₂F | Cl | SCH₃ | |
| 219 | CCl₂F | Cl | SC₂H₅ | |
| 220 | CCl₂F | Cl | SCH₂COOCH₃ | |
| 221 | CCl₂F | Cl | NHCH₃ | |

-continued $$\text{X} \underset{N}{\overset{Y}{\diagdown}} \text{—O—} \underset{NO_2}{\diagdown} \text{COB}$$

| No. | X | Y | B | Physical data (°C.) |
|---|---|---|---|---|
| 222 | CCl₂F | Cl | N(CH₃)₂ | |
| 223 | CClF₂ | Cl | OH | |
| 224 | CClF₂ | Cl | OCH₃ | |
| 225 | CClF₂ | Cl | OC₂H₅ | |
| 226 | CClF₂ | Cl | OC₃H₇ | |
| 227 | CClF₂ | Cl | OC₄H₉(iso) | |
| 228 | CClF₂ | Cl | OC₄H₉(sec) | |
| 229 | CClF₂ | Cl | SCH₃ | |
| 230 | CClF₂ | Cl | NHCH₃ | |
| 231 | CF₃ | Cl | N—OCH₃ <br> \| <br> CH₃ | |
| 232 | CF₃ | Br | OCH₃ | |
| 234 | CF₃ | Br | OC₂H₅ | |
| 235 | CF₃ | Br | OC₄H₉(iso) | |
| 236 | CF₃ | Br | OC₄H₉(sec) | |
| 237 | CF₃ | Br | SCH₃ | |
| 238 | CF₃ | Br | SC₃H₇(iso) | |
| 239 | CF₃ | Br | NHCH₂COOCH₃ | |
| 240 | CF₃ | Br | N(CH₃)₂ | |
| 241 | CF₃ | Br | OCH₂CH=CH₂ | |
| 242 | Cl | Cl | NHC(CH₃)₂CN | m.p. 160–162° |
| 243 | Cl | Cl | NHCH₂CH₂OCH₃ | m.p. 130–135° |
| 244 | Cl | Cl | O—⟨cyclopropyl⟩ | m.p. 96–99° |
| 245 | Cl | Cl | OCH(CH₃)C₅H₁₁ | $n_D^{27}$ 1.5600 |
| 246 | Cl | Cl | N(CH₃)OCH₃ | $n_D^{34}$ 1.6055 |
| 247 | Cl | Cl | OCH(CH₃)COOCH₂CH₃ | |
| 248 | Cl | Cl | SC₄H₉(sec) | $n_D^{27}$ 1.6000 |
| 249 | CF₃ | Cl | SCH₂COOCH₂CH₃ | |
| 250 | CF₃ | Cl | N(CH₃)OCH₃ | $n_D^{30}$ 1.5438 |
| 251 | CF₃ | Cl | NHSO₂CH₃ | m.p. 159–162° |
| 252 | CF₃ | Cl | O⊖Na⊕ | m.p. 200–201° |
| 253 | CF₃ | Cl | O⊖K⊕ | m.p. 152° deliquesces |

EXAMPLE 4

Preparation of a number of ready-for-use formulations and active ingredient concentrates:

Paste

The following substances are used to formulate a 45% paste:
45 parts of 2-nitro-5-(3',5'-dichloropyridyl-2'-oxy)benzoic acid,
5 parts of sodium aluminum silicate,
14 parts of cetyl polyglycol ether with 8 moles of ethylene oxide,
1 part of oleyl polyglycol ether with 5 moles of ethylene oxide,
2 parts of spindle oil,
10 parts of polyethylene glycol,
23 parts of water.

The active ingredient is intimately mixed with the additives in appropriate devices and ground. By diluting the resultant paste with water, it is possible to prepare suspensions of the desired concentration.

Emulsifiable Concentrate

The following ingredients are mixed to formulate a 25% emulsifiable concentrate:
25 parts of methyl 2-nitro-5-(3',5'-dichloropyridyl-2'-oxy)benzoate,
5 parts of a mixture of nonylphenolpolyoxyethylene and calcium dodecylbenzenesulfonate,
15 parts of cyclohexanone,
55 parts of xylene.

This concentrate can be diluted with water to give emulsions in suitable concentrations of e.g. 0.1 to 10%. Such emulsions are suitable for controlling weeds in crops of cultivated plants.

Wettable Powder

The following constituents are used to formulate (a) a 70% and (b) a 10% wettable powder:

(a)

70 parts of 2-nitro-5-(3',5'-dichloropyridyl-2'-oxy)benzoic acid isopropyl ester,
5 parts of sodium dibutylnaphthylsulfate,
3 parts of naphthalenesulfonic acid/phenolsulfonic acid/formaldehyde condensate (3:2:1),
10 parts of kaolin,
12 parts of Champagne chalk;

(b)

10 parts of the above compound,
3 parts of a mixture of the sodium salts of saturated fatty alcohol sulfates,
5 parts of naphthalenesulfonic acid/formaldehyde condensate,
83 parts of kaolin.

The indicated active ingredient is applied to the corresponding carriers (kaolin and chalk) and then these are mixed and ground, to yield wettable powders of excellent wettability and suspension power. By diluting these wettable powders with water it is possible to obtain suspensions containing 0.1 to 80% of active ingredient. These suspensions are suitable for controlling weeds in cultivations of plants.

EXAMPLE 5

The herbicidal activity of the compounds of the invention was determined by means of the following greenhouse tests:

Pre-emergence herbicidal activity (germination inhibition)

In a greenhouse, seeds of plants are sown in flower pots having a diameter of about 15 cm, such that 12–30 plants are able to develop in each pot. Directly after sowing the test plants, the surface of the soil is treated with an aqueous dispersion of active ingredient obtained from a 25% emulsifiable concentrate or from a 25% wettable powder with active ingredients which, because of insufficient solubility, cannot be formulated to emulsifiable concentrates. Four different concentration series are used, corresponding to 4, 2, 1 and 0.5 kg of active ingredient per hectare. The pots are kept in the greenhouse at 22°–25° C. and 50 to 70% relative humidity, and the test is evaluated after 3 weeks.

In this test, the compounds of the formula I at rates of application of 1 and 2 kg/ha are effective against the broad-leafed and also most grass-like weeds, whilst cultivated plants such as maize, and also to some extent wheat, millet, rice, soybeans and cotton, are not damaged or suffer only minor damage.

Post-emergence herbicidal activity (contact action)

A large number of weeds and cultivated plants (both monocots and dicots) are sprayed post-emergence in the 4- to 6-leaf stage with an aqueous active ingredient dispersion at rates of application of 0.5, 1, 2, and 4 kg/ha, and then kept at 24°–26° C. and 45–60% relative humidity. The test is evaluated after 3 weeks. In this test too, the compounds of formula I are thoroughly effective against the broad-leafed and most grass-like weeds at a rate of application of 1 kg/ha, whilst maize, barley, millet, rice, as well as cotton and soybeans are not damaged or are damaged only at higher rates of application.

What is claimed is:

1. 5-(3'-Chloro-5'-trifluoromethylpyridyl-2'-oxy)-2-nitrobenzoic acid allyl ester.
2. 5-(3'-Chloro-5'-trifluoromethylpyridyl-2'-oxy)-2-nitrobenzoic acid propynyl ester.
3. 5-(3',5'-Dichloropyridyl-2'-oxy)-2-nitrobenzoic acid allyl ester.
4. 5-(3',5'-Dichloropyridyl-2'-oxy)-2-nitrobenzoic acid buten-2-yl ester.
5. 5-(3',5'-Dichloropyridyl-2'-oxy)-2-nitrobenzoic acid propynyl ester.
6. 5-(3'-Chloro-5'-trifluoromethyl-2'-oxy)-2-nitrobenzoic acid buten-2-yl ester.
7. 5-(3'-Chloro-5'-trifluoromethyl-2'-oxy)-2-nitrobenzoic acid 2-methylpropen-2-yl ester.
8. 5-(3'-Bromo-5'-trifluoromethyl-2'-oxy)-2-nitrobenzoic acid allyl ester.
9. A herbicidal composition which contains, as active ingredient a herbicidally effective amount of a 5-(pyridyl-2'-oxy)-2-nitrobenzoic acid derivative according to claims 1, 2, 3, 4, 5, 6, 7 or 8.
10. A method of selectively controlling weeds in a crop of useful plants, which comprises applying to said crop a herbicidally effective amount of a compound according to claims 1, 2, 3, 4, 5, 6, 7 or 8.
11. A method according to claim 10, wherein the crop is a soybean crop.
12. A method according to claim 10, wherein the crop is a cereals crop.
13. A method according to claim 10, wherein the crop is a rice crop.

* * * * *